(12) United States Patent
Li et al.

(10) Patent No.: US 8,607,797 B2
(45) Date of Patent: Dec. 17, 2013

(54) AIRFLOW RESTRICTION SYSTEM

(75) Inventors: Kasey Kai-Chi Li, Palo Alto, CA (US);
Anant V. Hegde, Hayward, CA (US)

(73) Assignee: Kasey K. LI, East Palo Alto, CA (US)

( * ) Notice: Subject to any disclaimer, the term of this patent is extended or adjusted under 35 U.S.C. 154(b) by 803 days.

(21) Appl. No.: 12/852,374

(22) Filed: Aug. 6, 2010

(65) Prior Publication Data
US 2010/0331877 A1 Dec. 30, 2010

Related U.S. Application Data

(63) Continuation-in-part of application No. 12/408,605, filed on Mar. 20, 2009.

(51) Int. Cl.
*A61F 5/56* (2006.01)
(52) U.S. Cl.
USPC .......................................... 128/848; 600/538
(58) Field of Classification Search
USPC ............ 128/858, 848, 207.18; 602/6, 41, 52, 602/54; 606/201, 204.45; 600/538
See application file for complete search history.

(56) References Cited

U.S. PATENT DOCUMENTS

| 4,215,984 | A | 8/1980 | Reichley |
|---|---|---|---|
| 4,901,737 | A | 2/1990 | Toone |
| 4,995,404 | A | 2/1991 | Nemir |
| 5,232,362 | A | 8/1993 | Kanas |
| 5,373,859 | A | 12/1994 | Forney |
| 5,464,413 | A | 11/1995 | Siska, Jr. et al. |
| 5,513,986 | A | 5/1996 | Feltham et al. |
| 5,533,470 | A | 7/1996 | Rose |
| 5,915,385 | A | 6/1999 | Hakimi |
| 6,422,243 | B1 | 7/2002 | Daram |
| 6,494,209 | B2 | 12/2002 | Kulick |
| 6,675,804 | B1 | 1/2004 | Pivovarov |
| 6,722,360 | B2 | 4/2004 | Doshi |
| 6,877,513 | B2 | 4/2005 | Scarberry et al. |
| 6,955,172 | B2 | 10/2005 | Nelson et al. |
| 7,073,505 | B2 | 7/2006 | Nelson et al. |

(Continued)

FOREIGN PATENT DOCUMENTS

| WO | WO 2009/064914 | 5/2009 |
|---|---|---|
| WO | WO 2010/107461 | 9/2010 |
| WO | WO 2011/060103 | 5/2011 |

OTHER PUBLICATIONS

PCT International Patent Application No. PCT/US2009/069281 filed Dec. 22, 2009 in the name of Li, International Search Report mailed Mar. 11, 2010.

(Continued)

*Primary Examiner* — Patricia Bianco
*Assistant Examiner* — Camtu Nguyen
(74) *Attorney, Agent, or Firm* — Levine Bagade Han LLP

(57) ABSTRACT

Airflow restriction systems are described herein which may be used to treat various disorders by creating expiratory positive airway pressure while providing for patient comfort regardless of the patient's anatomical variances. Such a device may be removably secured externally over the patient's nose rather than within the nasal passages to increase patient comfort. The restriction device may be secured, e.g., via an adhesive, to the patient and actuated via any number of mechanical or electromechanical mechanisms. Moreover, the restriction device may include one or more sensors to detect the patient's respiration activity such that the device may be actuated to correspond to the patient's exhalation and squeeze or otherwise constrict the nasal passages at least partially by pressing against the exterior surface of the nose to restrict the expiratory airflow.

15 Claims, 13 Drawing Sheets

(56) References Cited

U.S. PATENT DOCUMENTS

| | | |
|---|---|---|
| 7,334,581 B2 | 2/2008 | Doshi |
| 7,607,439 B2 | 10/2009 | Li |
| 7,954,494 B1 | 6/2011 | Connor |
| 2001/0047805 A1 | 12/2001 | Scarberry et al. |
| 2002/0144685 A1 | 10/2002 | Ivanovich et al. |
| 2004/0045555 A1 | 3/2004 | Nelson et al. |
| 2004/0045556 A1 | 3/2004 | Nelson et al. |
| 2004/0049102 A1 | 3/2004 | Nelson et al. |
| 2004/0122456 A1 | 6/2004 | Saadat et al. |
| 2004/0194780 A1 | 10/2004 | Doshi |
| 2006/0000472 A1 | 1/2006 | Fenton |
| 2006/0005843 A9 | 1/2006 | Nelson et al. |
| 2006/0032497 A1 | 2/2006 | Doshi |
| 2006/0096600 A1 | 5/2006 | Witt et al. |
| 2006/0144398 A1 | 7/2006 | Doshi et al. |
| 2006/0150978 A1 | 7/2006 | Doshi |
| 2006/0150979 A1 | 7/2006 | Doshi et al. |
| 2007/0277832 A1 | 12/2007 | Doshi |
| 2007/0283962 A1 | 12/2007 | Doshi et al. |
| 2007/0289600 A1 | 12/2007 | Li |
| 2007/0295338 A1 | 12/2007 | Loomas et al. |
| 2008/0041373 A1 | 2/2008 | Doshi et al. |
| 2009/0120446 A1 | 5/2009 | Vaska et al. |
| 2009/0120447 A1 | 5/2009 | Vaska et al. |
| 2009/0123886 A1 | 5/2009 | Vaska |
| 2010/0000551 A1 | 1/2010 | Li |
| 2010/0241159 A1 | 9/2010 | Li |
| 2010/0288288 A1 | 11/2010 | Hegde et al. |
| 2010/0294283 A1 | 11/2010 | Li |
| 2010/0326448 A1 | 12/2010 | Li |
| 2011/0180076 A1 | 7/2011 | Hegde et al. |

OTHER PUBLICATIONS

Colrain, I.M. et al., "A Pilot Evaluation of a Nasal Expiratory Resistance Device for the Treatment of Obstructive Sleep Apnea," *J Clin Sleep Med*, vol. 4(5): 26 pages, 2008.

AIRFLOW RESTRICTION SYSTEM

CROSS-REFERENCE TO RELATED APPLICATIONS

This is a continuation-in-part of U.S. patent application Ser. No. 12/408,605 filed Mar. 20, 2009, which is incorporated herein by reference in its entirety.

FIELD OF THE INVENTION

The present invention relates to apparatus and methods for controlling airflow through nasal passages of a patient. More particularly, the present invention relates to methods and apparatus for controllably restricting airflow through the nasal passages of the patient for the treatment of various disorders such as snoring, obstructive sleep apnea (OSA), chronic obstructive pulmonary disease (COPD), asthma, heart failure, etc.

BACKGROUND OF THE INVENTION

In treating various disorders such as snoring, OSA, COPD, asthma, heart failure, etc., therapies such as pulmonary rehabilitation or mechanical ventilation are typically employed. Pulmonary rehabilitation generally involves educating the patient and having them perform various exercises to reduce symptoms and to decreases the disability by helping to condition pulmonary muscles and increase inspiratory tidal volumes. However, such pulmonary rehabilitation exercises require that the patient consciously perform them and they cannot be done while the patient is asleep.

In pulmonary rehabilitation as well as mechanical ventilation devices may aid facilitating the inspiration of air but also provide expiratory resistance in delaying the expiration of air from the patient's lungs. This expiratory delay not only decreases the patient's respiration rate, but the delayed retention of air within the lungs may also facilitate gaseous exchange to improve oxygen saturation levels as well as reduce symptoms of snoring, OSA, COPD, asthma, heart failure, etc.

Treatments such as mechanical ventilation machines are generally utilized to treat respiratory disorders such as OSA. In use, a mask is placed over the patient's nose and/or mouth or nasal pillows are positioned within the nostrils of the patient and air is delivered at a continuous positive pressure into the airways of the patient to prevent or inhibit the upper airways from collapsing during sleep. Such devices, known as continuous positive airway pressure (CPAP) devices may be set a constant pressure level or they may be set at differing pressure levels. However, many patients have difficulties in adjusting to CPAP devices for various reasons.

Yet another treatment involves the placement of airflow resistance devices directly within the nostrils or nasal passages of the patient. These devices are generally removably secured within the nostrils by resistance or within the mouth and incorporate a valve to provide for inspiration of air but provides for increased resistance to expiration to create a positive pressure ventilation. However, such devices requiring securement, e.g., within the nostrils, may be uncomfortable for the user to wear and may also provide a poor fit depending upon the anatomy of the patient's nasal passages.

Accordingly, there is a need for a system which can create expiratory positive airway pressure to treat various conditions while providing for patient comfort regardless of the patient's anatomical variances.

BRIEF SUMMARY OF THE INVENTION

A device which can create expiratory positive airway pressure may be utilized to treat various disorders, e.g., snoring, OSA, COPD, asthma, heart failure, etc., while providing for patient comfort regardless of the patient's anatomical variances. Such a device may be optionally disposable and may be removably secured externally over the patient's nose rather than within the nasal passages to increase patient comfort. The restriction device may be secured, e.g., via an adhesive, to the patient and actuated via any number of mechanical or electromechanical mechanisms. Moreover, the restriction device may include one or more sensors to detect the patient's respiration activity such that the device may be actuated to correspond to the patient's exhalation and squeeze or otherwise constrict the nasal passages at least partially by pressing against the exterior surface of the nose to restrict the expiratory airflow.

One variation of the restriction device may include a first support member and a second support member coupled to one another via an actuatable bridge. The first and second support members may each have a respective contact surface which may each have an adhesive for temporarily securing to the patient's skin surface. Moreover, support members may also comprise various electronic components as well (e.g., a power supply, receiver, processor, etc.) for controlling the actuation of the bridge. When the bridge is actuated, it may bend or constrict to urge or draw the support members towards one another in a first direction. When the bridge is relaxed or reconfigured into a second configuration, the support members may relax or move in a second direction opposite to the first direction where the support members move away from one another back to their initial position.

The actuatable bridge may be comprised of any number of mechanisms to impart the reconfiguration from a relaxed first configuration to a constricting second configuration. For example, the bridge may comprise an electromechanical mechanism such as an electromagnet integrated along the length of the bridge such that passing a current through the bridge magnetizes opposing portions of the bridge to draw and/or repel them towards or away from one another. Alternatively, the bridge may integrate an electroactive polymer strip or portion which reconfigures between a relaxed and constricted configuration when energized to alternate between the configurations described above. Other constricting mechanisms, such as inflation reservoirs may also be utilized.

In use, the restriction device may be placed over a patient's nose when the bridge is relaxed or non-activated. For example, the support members may be securely adhered either directly upon the patient's nose or upon the skin adjacent to the nose on either side such that the bridge is relaxed upon or inferior to the nasal bridge and superior to the nasal openings (nostrils). The bridge may be positioned anywhere along the surface of the nose provided that when bridge reconfigures into its restricted shape, the underlying nasal passages through the nose may become at least partially constricted. With the bridge secured upon the nose by the support members, the bridge may be actuated to constrict, as previously described, such that the underlying nasal passages become restricted anywhere from 1 to 10 mm. Thus, the air to be exhaled through the nasal openings is restricted accordingly and exhalation airflow is reduced to create an expiratory positive airway pressure state in the patient.

Because the nasal passages are desirably constricted upon patient exhalation while remaining unimpeded during inhalation, the restriction device may comprise one or more sensors to detect and distinguish between patient inhalation and exhalation. Such sensors may comprise any number of detection mechanisms, e.g., temperature sensors to detect warm air exhaled from the patient, airflow sensors to detect exhalation activity, etc. The sensors may be electrically coupled to a processor contained, e.g., either in the members or wirelessly to an externally based processor. As the patient inhales air, the restriction device may remain un-activated. However, as the patient exhales, the one or more sensors may detect the exhalation activity and the restriction device may be actuated automatically to constrict the underlying nasal passages until exhalation activity is no longer detected, in which case the device may automatically relax to allow the nasal passages to re-open.

Other variations of the device may include restriction devices incorporated with one or more sensors positioned upon contoured or curved supports as well as support members which may be coupled to one another via a hinge or pivot mechanism. Additional variations may also include systems where a sensing assembly may be unattached to the restriction device but remain in communication, e.g., wirelessly, with one another.

In yet other variations, a portion of the restriction device may be positioned directly within the nasal passages. A nasal clip or attachment may extend across and partially within the nasal openings with extended shutter or flap members extending between the attachments and the central clip or attachment. The shutter or flap members may comprise a movable member which may be rotated or otherwise constricted between a deployed and retracted configuration. In its deployed configuration, exhalation of air may be constricted by the deployed members narrowing the nasal openings. During inhalation, the members maybe reconfigured into a retracted shutter or flap to allow for air to pass relatively unimpeded during inhalation. In this variation, the members may be comprised of a reconfigurable electroactive polymer which may reconfigure itself when a current is applied.

Yet another variation of a restriction device may be positioned directly within the nasal openings where the restriction members may comprise electroactive polymers (e.g., formed into C-shaped, circular, ovular, etc. structures) which expand to reconfigure themselves. In use, each of the restriction members may be positioned within a respective nasal opening such that they present an obstruction to airflow through the openings but when actuated, e.g., during inhalation, they may widen to expand the nasal openings to allow for increased airflow. Another variation may utilize reconfigurable restriction members which extend and contract to alter airflow resistance accordingly.

In yet another variation, the restriction device may be adhered onto the patient's nose. However, rather than the device constricting, it may function to anchor the constricting member which may extend along the nose and around the tip of the nose. For a patient with an otherwise constricted nasal passage, the constricting member (which may be comprised of a reconfigurable electroactive polymer) may be actuated to constrict such that the member may pull on the tip of the nose to increase the airflow through the nasal openings.

In another example, a fluid or gas may be actuated between a reservoir and inflatable respective first and second restriction elements to partially constrict the airflow through the patient's nasal passages. A fluid lumen may connect the reservoir with the restriction elements and the first and/or second actuatable members may be positioned along a surface or within the reservoir such that when the actuatable members are actuated to squeeze or constrict, the fluid contained within the reservoir may be forced or urged out and into the respective first and second inflated restriction members such that inflation of these members constrict the underlying nasal passages to induce the expiratory positive airway pressure. During inhalation, the actuatable members may be relaxed to allow the fluid to flow back from the members into the reservoir. To facilitate the fluid transfer, the members may be made from a distensible material, such as latex, which may be inflated yet is biased to collapse to urge the fluid back into the reservoir.

DETAILED DESCRIPTION OF THE INVENTION

In treating various disorders, e.g., snoring, OSA, COPD, asthma, heart failure, etc., a device which can create expiratory positive airway pressure may be utilized which provides for patient comfort regardless of the patient's anatomical variances. Generally, such a device may be optionally disposable and may be removably secured externally over the patient's nose rather than within the nasal passages to increase patient comfort. The restriction device may be secured, e.g., via an adhesive, to the patient and actuated via any number of mechanical or electromechanical mechanisms. Moreover, the restriction device may include one or more sensors to detect the patient's respiration activity such that the device may be actuated to correspond to the patient's exhalation and squeeze or otherwise constrict the nasal passages at least partially by pressing against the exterior surface of the nose to restrict the expiratory airflow.

Figure 1A:
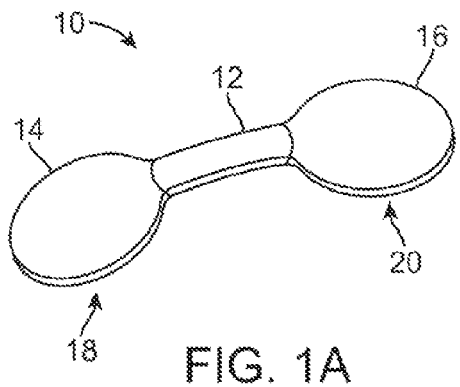
FIGS. 1A to 1C show perspective and respective side views of one variation of an airflow restriction device which may be actuated to constrict a patient's airflow through their nasal passages.

As shown in the perspective view of FIG. 1A, one variation of restriction device 10 is illustrated where a first support member 14 and a second support member 16 may be coupled to one another via an actuatable bridge 12. First and second support members 14, 16 may each have a respective contact surface 18, 20 which may each have an adhesive for temporarily securing to the patient's skin surface. Moreover, support members 14, 16 may also comprise various electronic components as well (e.g., a power supply, receiver, processor, etc.) for controlling the actuation of bridge 12.

Figure 1B:
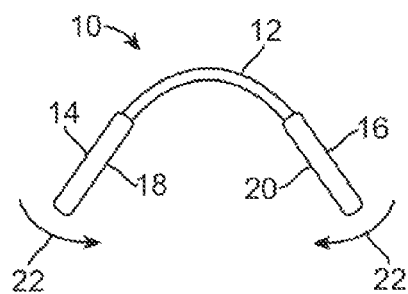
Figure 1C:
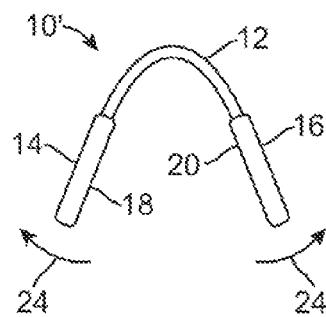

FIGS. 1B and 1C illustrate side views of restriction device 10 in a relaxed configuration and a constricted configuration, respectively. When bridge 12 is in a relaxed or first configuration, support members 14, 16 may rest upon the patient's nose with bridge 12 taking a curved or arcuate shape. When bridge 12 is actuated, bridge 12 may bend or constrict to urge or draw support members 14, 16 towards one another in a first direction 22, as shown by the constricted device 10' in FIG. 1B. When bridge 12 is relaxed or reconfigured into a second configuration, support members 14, 16 may relax or move in a second direction 24 opposite to the first direction where support members 14, 16 move away from one another back to their initial position, as shown in FIG. 1C.

Actuatable bridge 12 may be comprised of any number of mechanisms to impart the reconfiguration from a relaxed first configuration to a constricting second configuration. For example, bridge 12 may comprise an electromechanical mechanism such as an electromagnet integrated along the length of bridge 12 such that passing a current through bridge 12 magnetizes opposing portions of bridge 12 to draw and/or repel them towards or away from one another. Alternatively, bridge 12 may integrate an electroactive polymer strip or portion which reconfigures between a relaxed and constricted configuration when energized to alternate between the configurations described above. Other constricting mechanisms, such as inflation reservoirs may also be utilized, as described in further detail below.

Figure 2A:
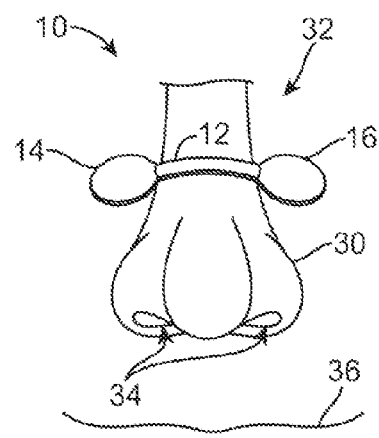
FIGS. 2A and 2B show an example of a device adhered over a patient's nose, e.g., inferior to the bridge of the nose, such that actuation of the device partially constricts the nasal passages to at least partially restrict the airflow during exhalation.

In use, restriction device 10 may be placed over a patient's nose 30 when bridge 12 is relaxed or non-activated. For example, support members 14, 16 may be securely adhered either directly upon the patient's nose 30 or upon the skin adjacent to the nose 30 on either side, as shown in FIG. 2A, such that bridge 12 is relaxed upon or inferior to the nasal bridge 32 and superior to nasal openings (nostrils) 34. In other variations described herein, bridge 12 may also be utilized with other components positioned superior to mouth 36. Bridge 12 may be positioned anywhere along the surface of the nose 30 provided that when bridge 12 reconfigures into its restricted shape, the underlying nasal passages through nose 30 may become at least partially constricted.

Figure 2B:
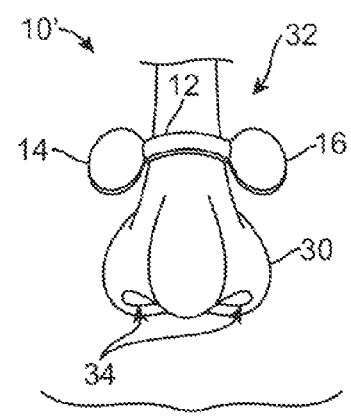

With bridge 12 secured upon nose 30 by support members 14, 16, bridge 12 may be actuated to constrict, as previously described, such that the underlying nasal passages become restricted by bridge 12 and/or members 14, 16 anywhere from 1 to 10 mm. Thus, the air to be exhaled through nasal openings 34 is restricted accordingly and exhalation airflow is reduced to create an expiratory positive airway pressure state in the patient, as shown in FIG. 2B.

Figure 2C:
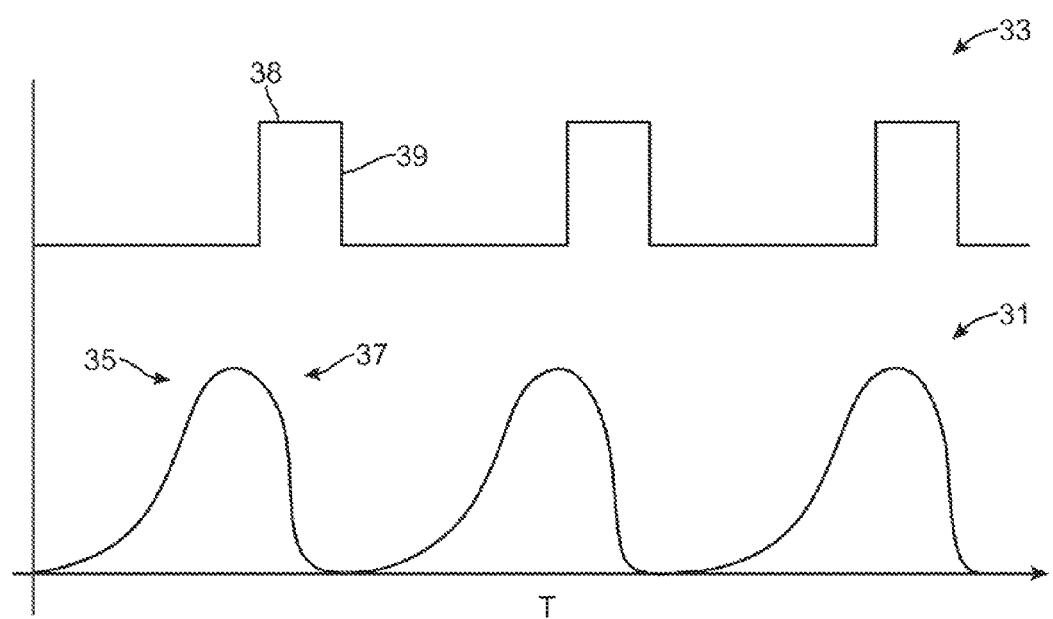
FIG. 2C illustrates a chart of a patient's respiration activity and the corresponding actuation of the restriction device to create expiratory positive airway pressure.

Because the nasal passages are desirably constricted upon patient exhalation while remaining unimpeded during inhalation, restriction device 10 may comprise one or more sensors to detect and distinguish between patient inhalation and exhalation. Such sensors may comprise any number of detection mechanisms, e.g., temperature sensors to detect warm air exhaled from the patient, airflow sensors to detect exhalation activity, etc. The sensors may be electrically coupled to a processor contained, e.g., either in member 14 or 16 or wirelessly to an externally based processor. As shown in the chart of FIG. 2C, a patient's exemplary respiration activity 31 is illustrated indicating inhalation 35 and exhalation 37 over a time period, T, and the corresponding restriction device actuation 33 is illustrated above. As the patient inhales air 35, the restriction device 10 may remain un-activated. However, as the patient exhales 37, the one or more sensors may detect the exhalation activity and restriction device 10 may be actuated 38 automatically to constrict the underlying nasal passages until exhalation activity 37 is no longer detected, in which case device 10 may automatically relax 39 to allow the nasal passages to re-open.

This process of constriction and relaxation may be repeated until the patient de-activates the device 10. Alternatively, device 10 may be optionally programmed to activate after a preset time period and/or to de-activate automatically as well. Moreover, device 10 may be programmed to constrict bridge 12 in a stepped manner over a predetermined time period. For example, bridge 12 may be programmed to constrict 0 mm for the first 15 minutes after activation and then constrict 1 mm for the subsequent 15 minutes and then constrict more than 1 mm for another subsequent time period, etc. Additionally, because the device may be used when the patient is either awake or asleep, device 10 may be programmed to have a fail-safe feature where the device 10 automatically relaxes or releases in the event of any failures such that the nasal passages remain un-constricted until the patient is able to remove the device 10.

Figure 2D:
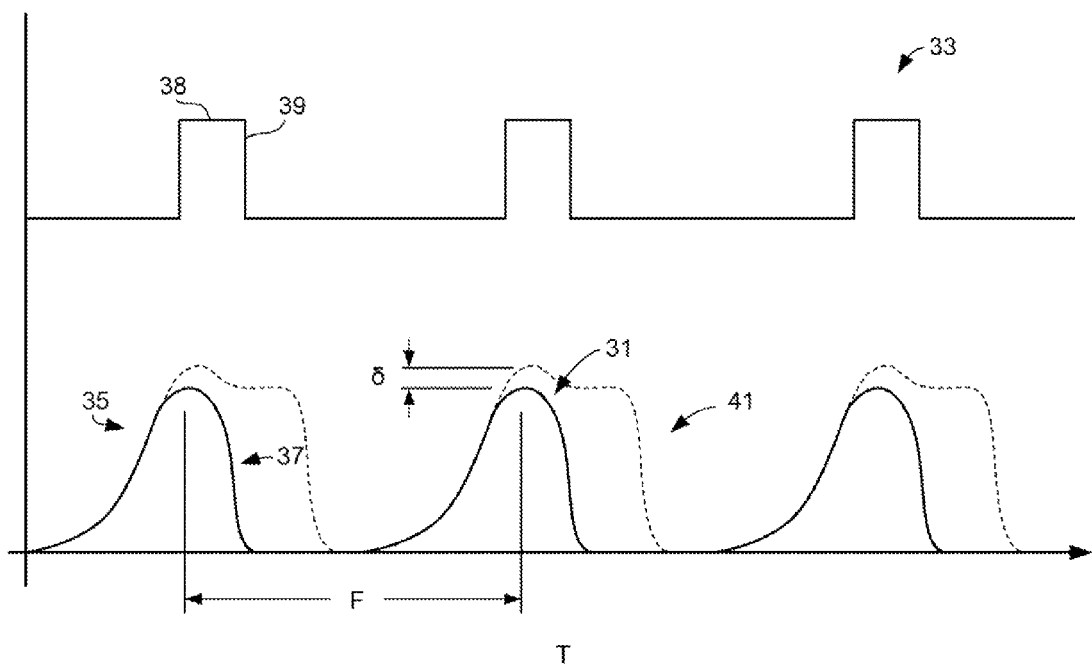
FIG. 2D illustrates a chart of a breathing pattern altered by extending the period of exhalation utilizing the devices and methods described.

As shown in the chart of FIG. 2D, the exhalation activity 37 of the patient may show how the device 10 may alter the breathing pattern of the patient by extending the period of exhalation 37 such that an extended exhalation 41 pattern results. Thus, the duration of the exhalation may be increased when actuated, as indicated by actuation 33, relative to the duration of exhalation which would normally occur without use of the device. Because of the increased exhalation duration and the dwell time of the volume of air retained within the lungs and nasal passages, various sleep disordered breathing symptoms may be treated accordingly.

The pump and/or actuator may be configured to actuate over a variable range of time, e.g., a minimum dwell time of 500 ms to a maximum dwell time of 1500 ms, and the device 10 may be set to optionally increase or ramp its actuation time by a preset interval, such as at 50 ms increments. Thus, the processor may receive data from flow sensor (or any other triggering sensor) and accordingly initiate the device 10 to actuate at a first time interval, e.g. 500 ms upon detection of a patient's exhalation. This time interval may be increased or ramped up to a maximum of, e.g., 1500 ms.

In determining the length of time which the device may be actuated, the patient's breathing frequency can be recorded and time-averaged over, e.g., the previous five breathing cycles, by the processor to calculate a running average which may be constantly updated. The processor may accordingly initiate actuation of the device to restrict the patient's air passage, as described herein, while sensing the altered breathing frequency and tidal volume. The processor may then calculate the difference, $\delta$, between the modified inhalation volume and the unaltered volume to determine whether the breathing is assisted or unassisted. The difference, $\delta$, may be continually updated depending upon the calculated running average detected with respect to the modified exhalation pattern 41 such that changes in $\delta$ may then be considered by the processor in either increasing or decreasing the actuation time of the device. Any of the processors, sensors, and various actuation mechanisms described herein may be utilized accordingly.

Figure 3:
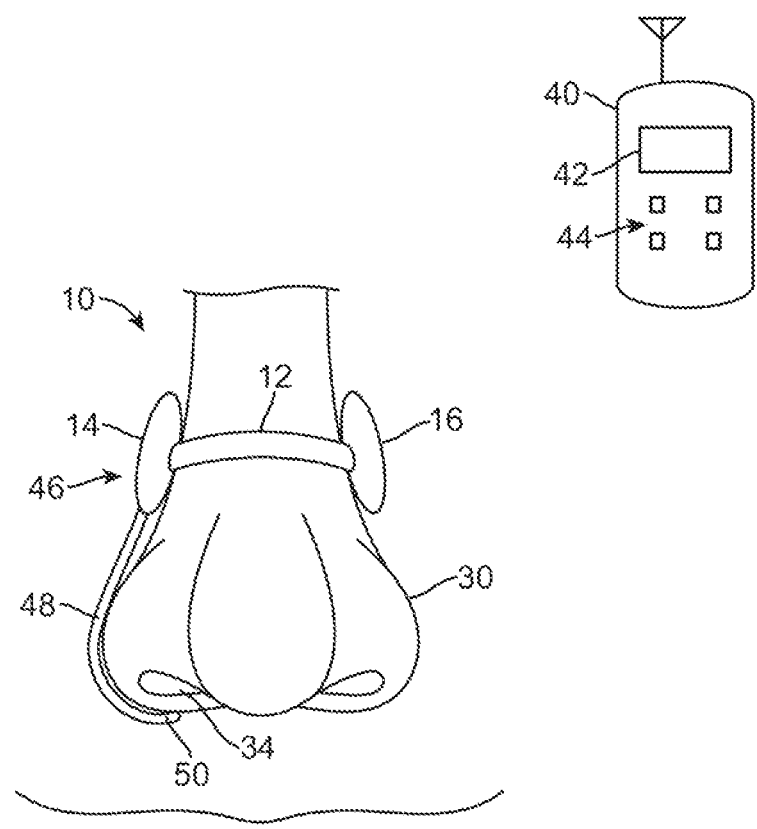
FIG. 3 shows an example of a variation where the device may incorporate a sensor to detect inhalation and exhalation of the patient as well as a controller to control various aspects of the device.

The one or more sensors may be incorporated with device 10 in various configurations. As shown in FIG. 3, a wire or conformable member 48 may extend from support member 14 and/or 16 to a location where sensor 50, which is positioned on a distal end of member 48, may be located proximate to nasal opening 34 to detect the airflow, temperature, or other physiological parameter of the patient. Also shown is an optional controller 40 which may be in wireless (or wired) communications with an electronics assembly 46 via a receiver or transmitter optionally integrated within support member 14 and/or 16. Controller 40 may be configured in a variety of ways and may include a display 42 for indicating any number of parameters or information as well as control pad 44 for providing user input. Alternatively, controller 40 may be integrated with any number of other devices, e.g., PDA, cell phone, watch, etc.

Figure 4A:
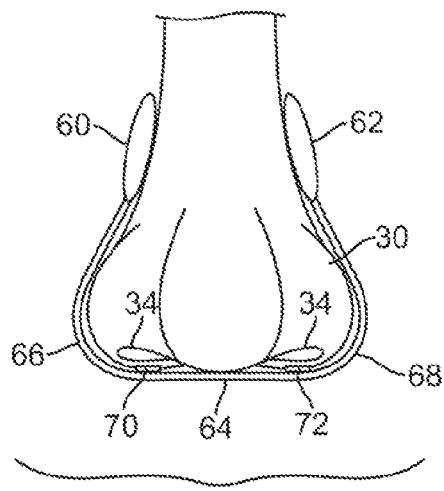
FIGS. 4A and 4B show front and side views, respectively, of another variation of the device positioned upon a patient's nose with one or more sensors in proximity to the nasal passages.
Figure 4B:
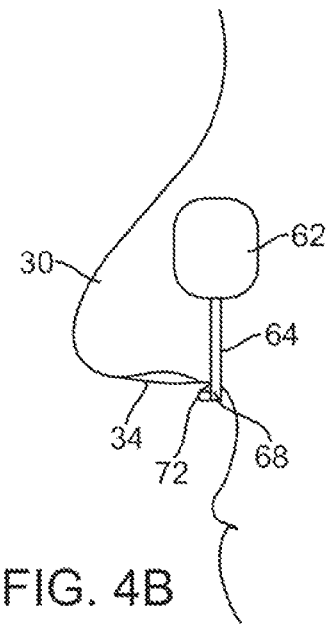

Another variation of the device is shown in the front and side views of FIGS. 4A and 4B, respectively. As illustrated, first support 60 and second support 62 may be secured on either side of nose 30 while actuating bridge 64 may extend and rest along the inferior contour of nose 30 posterior to the nasal openings 34 and superior to the mouth 36 of the patient. Actuating bridge 64 may be accordingly contoured or curved 66, 68 and one or more sensors 70, 72 may be positioned along bridge 64 adjacent to the nasal openings 34 for detecting exhalation activity. In this manner, bridge 64 may be actuated to urge or draw apposed supports 60, 62 towards one another accordingly.

Figure 5A:
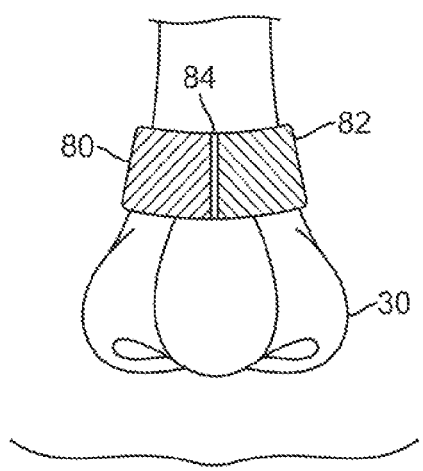
FIGS. 5A and 5B show front and side views, respectively, of yet another variation of the device which may flex or articulate via a hinge or pivot.
Figure 5B:
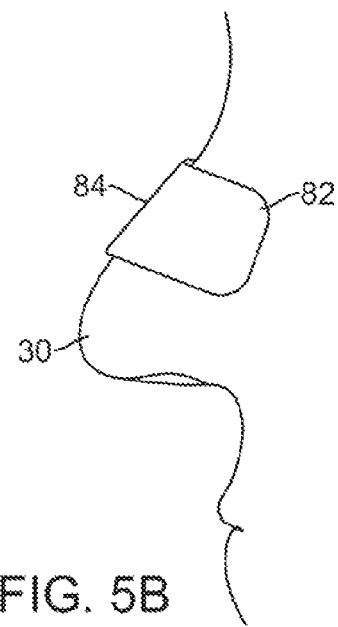

FIGS. 5A and 5B show front and side views, respectively, of another variation of the device where first support 80 and second support 82 are integrated and joined to one another via a hinge or pivot 84 mechanism to form a continuous structure. In this manner, supports 80, 82 may be adhered or fitted onto the patient's nose 30 like a clip mechanism while supports 80, 82 may be secured to nose 30 via an adhesive to via a clamping force. Hinge or pivot 84 may be comprised of an actuating mechanism, as described above, to urge or draw supports 80, 82 towards one another or a separate actuating mechanism may be placed over or upon supports 80, 82 to provide the biasing force to effect constriction.

Figure 6:
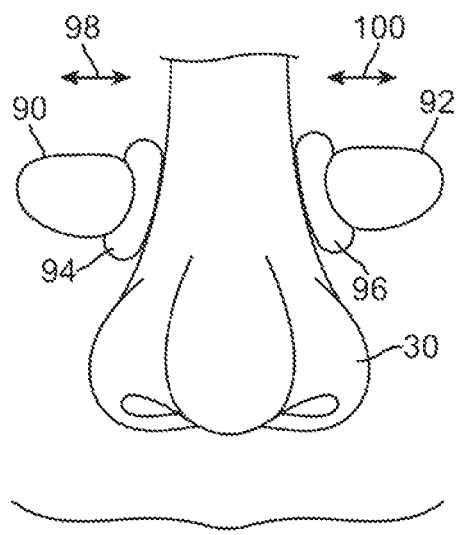
FIG. 6 shows a front view of yet another variation where one or more components may be positioned in apposition against one or both sides of the patient's nose to at least partially constrict airflow.

FIG. 6 shows a front view of yet another variation where first support 90 and second support 92 may be secured along either side of nose 30 such that the supports 90, 92 are unattached to one another. First support 90 may comprise a first actuator 94 in contact against a first surface of the nose 30 while second support 92 may comprise a second actuator 96 in contact against a second surface of the nose 30 opposite to the first surface. One or both actuators 94, 96 may be activated to press against the respective surface of the nose 30 as indicated by the direction of constriction 98 and 100, respectively. Because the supports and actuators are unattached to one another, actuators 94, 96 may be in wireless communication with one another or with an external controller to coordinate their movement. Alternatively, a single support and actuator may be utilized against a single corresponding nasal passage, if so desired.

Figure 7A:
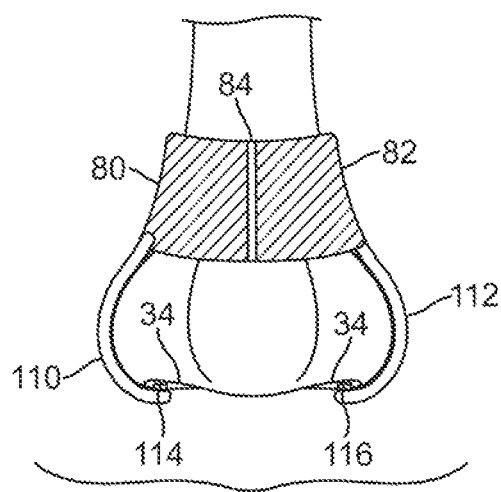
FIGS. 7A and 7B show front and inferior side views, respectively, of yet another variation having one or more sensors which may be positioned directly within a respective nostril.
Figure 7B:
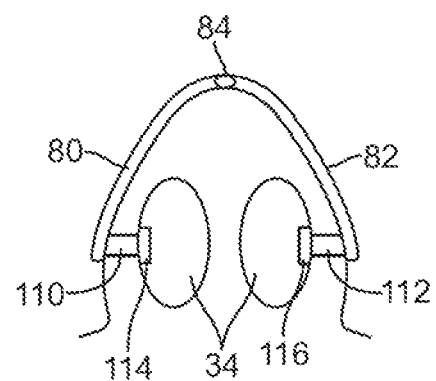

FIGS. 7A and 7B show front and inferior views, respectively, of yet another variation where the device previously described above having first support 80 and second support 82 may further include a first member 110 extending from first support 80 and a second member 112 extending from second support 82. Each support may include a respective first sensor 114 and second sensor 116 which may extend proximate to or partially within the nasal openings 34 for providing respiratory sensing to the device.

Figure 8:
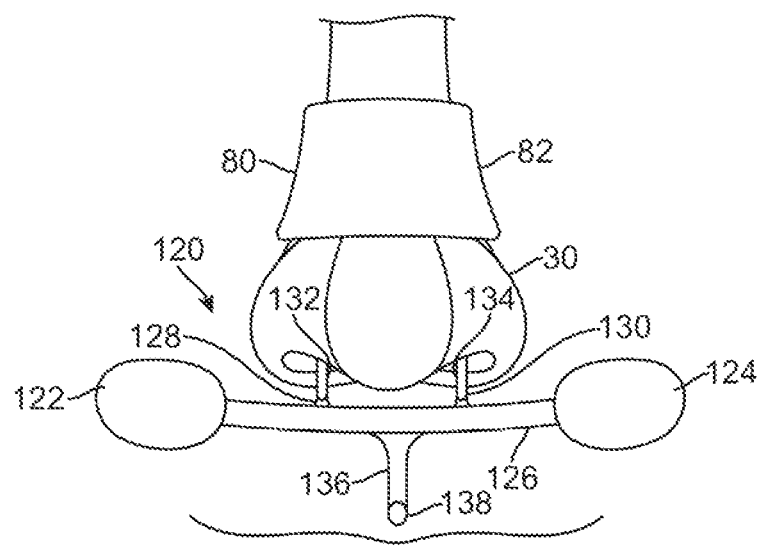
FIG. 8 shows a front view of another variation where a restriction device may be positioned along the patient's nose and a separate sensor may be positioned between the nose and mouth of the patient for detecting one or more physiological parameters.

Yet another variation is shown in the front view of FIG. 8, which illustrates a restriction device positioned upon the nose 30 and a separate sensing assembly 120 which may be unattached to the restriction device. Any of the restriction device variations shown herein may be utilized with the sensing assembly 120 as practicable, if so desired. As above, sensing assembly 120 may remain in communication, e.g., wirelessly, with the device and/or with an external controller. In either case, this example illustrates a sensing assembly 120 having a first support 122 and a second support 124 with a connecting member 126 extending therebetween. Supports 122, 124 may be temporarily adhered to the skin surface such that connecting member 126 extends between the patient's nose 30 and mouth. A first member 128 having a first sensor 132 may be extend proximate to or partially within a first nasal passage and an optional second member 130 having a second sensor 134 may also extend proximate to or partially within a second nasal passage. Additionally, an optional third member 136 having a third sensor 138 may extend towards the mouth of the patient to detect respiration or other physiological parameters from the patient's mouth.

Figure 9A:
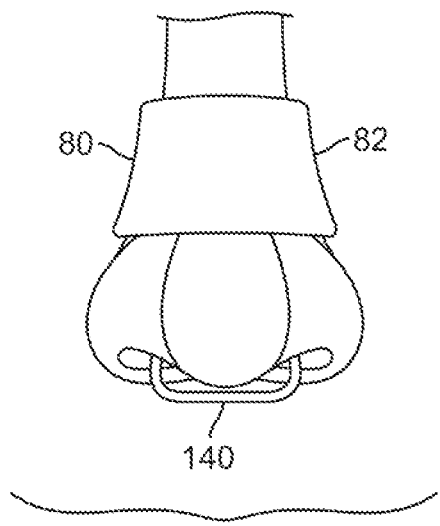
FIGS. 9A and 9B show front and inferior side views, respectively, of another variation where a restriction device may be positioned along the patient's nose and a separate sensor may be positioned along the nasal septum.
Figure 9B:
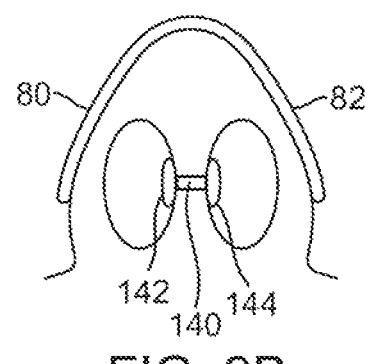

FIGS. 9A and 9B show another variation in front and inferior views where the restriction device may be positioned upon or over the patient's nose 30, as previously described, along with a separate and unattached connecting member 140. In this variation, connecting member 140 may have a first sensor 142 and an optional second sensor 144 each positioned proximate to or partially within a respective nasal opening. Connecting member 140 may be clipped to the nasal septum to secure it in place or otherwise adhered.

Figure 10A:
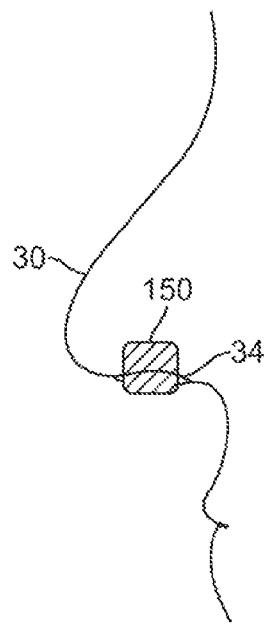
FIG. 10A shows a side view of yet another variation where airflow-restrictive elements may be positioned proximate to the nasal passages.
Figure 10B:
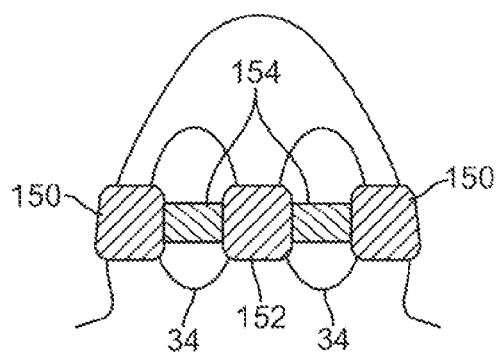
FIGS. 10B and 10C show inferior views of the airflow-restrictive elements actuated between a restrictive and a non-restriction configuration, respectively.
Figure 10C:
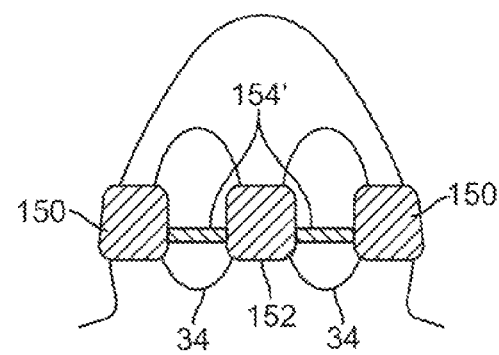

In yet other variations, a portion of the restriction device may be positioned directly within the nasal passages. As shown in the side and inferior views of FIGS. 10A to 10C, nasal clip or attachment 150 may extend across and partially within the nasal openings 34 with extended shutter or flap members 154 extending between attachments 150 and central clip or attachment 152. Shutter or flap members 154 may comprise a movable member which may be rotated or otherwise constricted between a deployed and retracted configuration. In its deployed configuration, shown in FIG. 10B, exhalation of air may be constricted by the deployed members 154 narrowing the nasal openings 34. During inhalation, the members 154 maybe reconfigured into a retracted shutter or flap 154', as shown in FIG. 10C, to allow for air to pass relatively unimpeded during inhalation. In this variation, members 154 may be comprised of a reconfigurable electroactive polymer which may reconfigure itself when a current is applied.

Figure 11A:
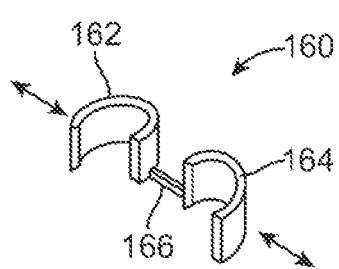
FIGS. 11A and 11B show perspective and inferior views, respectively, of yet another variation where the restrictive device may be positioned within the nasal passages and functions to expand or contract the nasal openings.
Figure 11B:
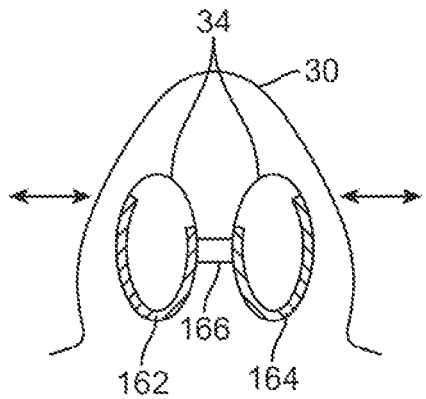

FIGS. 11A and 11B show perspective and inferior views, respectively, of yet another variation of a restriction device 160 which may be positioned directly within the nasal openings 34. Device 160 may comprise a first restriction member 162 and a second restriction member 164 coupled to one another via a connecting bridge 166. Restriction members 162, 164 may comprise electroactive polymers (e.g., formed into C-shaped, circular, ovular, etc. structures) which expand to reconfigure themselves, as indicated in FIG. 11A. In use, each of the restriction members 162, 164 may be positioned within a respective nasal opening 34 with bridge 166 extending therebetween. With the restriction members 162, 164 positioned accordingly, they may present an obstruction to airflow through the openings 34 but when actuated, e.g., during inhalation, they may widen to expand the nasal openings 34 to allow for increased airflow, as indicated in FIG. 11B.

Figure 12A:
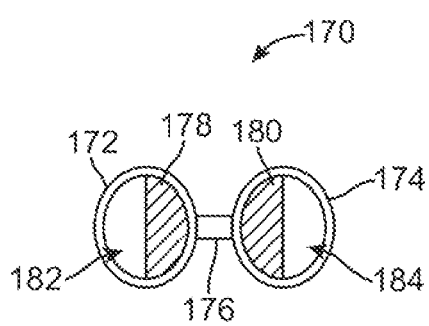
FIGS. 12A and 12B show side views of another variation where one or more restrictive elements may be actuated between a partially closed and opened configuration, respectively.
Figure 12B:
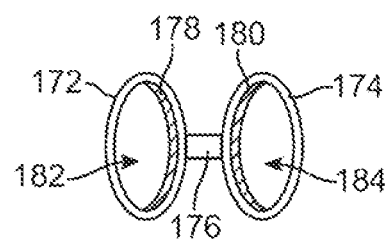

FIGS. 12A and 12B show yet another variation of an example in which restriction device 170 may be formed (e.g., C-shaped, circular, ovular, etc. structures) having a first restriction member 172 and a second restriction member 174 coupled to one another via a connecting bridge 176. Each of the restriction members 172, 174 may define a corresponding first and second airway 182, 184 therethrough with each having a respective first and second reconfigurable obstruction 178, 180 positioned within. During exhalation, obstructions 178, 180 may be deployed to restrict the respective airways, as shown in FIG. 12A. During inhalation, the obstructions 178, 180 may be urged, activated, or otherwise actuated to reconfigure into a low-profile shape such that the airways 182, 184 are relatively unimpeded, as shown in FIG. 12B. Actuation of the obstructions 178, 180 may be done automatically, as previously described.

Figure 13:
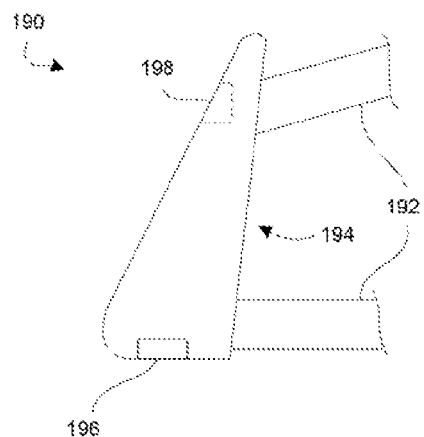
FIG. 13 shows a side view of a housing which may be positioned over the nose of the patient and which incorporates a restricting valve assembly.

In yet another variation, the restriction device may be placed in proximity to the nasal passages by incorporating a restricting valve assembly 196 within a housing 194 which may be placed entirely or at least partially over the nose of the user, as shown by side view of the assembly 190 in FIG. 13. The housing 194 may be sized for placement over the entire nose of the user, in this example, and held in place over the nose by one or more straps 192 which may be placed over and behind the user's head. A seal may be formed around the periphery of the housing 194 when secured against the user such that the valve assembly 196 is positioned in proximity to the user's nostrils. An example of a housing 194 may be seen in U.S. patent application Ser. No. 11/805,496 filed May 22, 2007 (U.S. Pat. Pub. 2007/0277832), which is incorporated herein by reference in its entirety.

The housing 194 may also optionally incorporate an electronics assembly 198 directly within the housing 194 allowing the electronics assembly 198 to be in wired or wireless communication with the valve assembly 196. In other variations, the electronics assembly 198 may be omitted from the housing 194 and instead be positioned remotely from the housing 194 and patient. The valve assembly 196 integrated within the housing 194 may incorporate one or more valve leaflets to form a valve where the inflow of air through the valve assembly 196 and into the housing 194 is allowed at a first flow rate while the outflow of air through the valve assembly 196 from the housing is at least partially restricted at a second flow rate which is less than the first flow rate to achieve restricted exhalation, as described herein.

The valve assembly 196 may have various configurations which may utilize, for instance, electroactive polymers which may allow for a relatively higher flow rate in a first direction but stiffen when electrically actuated where the air flows in a second opposite direction, such as when breathing out. Moreover, the degree of stiffening may be varied to accommodate different airflow rates for differing patient conditions and anatomies.

Additionally, the activation of the electroactive polymer to alter the degree of stiffening may be delayed, e.g., by 15 to 45 minutes after activation by the patient to increase patient comfort. The activation may be preset either manually or automatically in which case the activation may occur upon the trigger of the device by the detection of disordered breathing. Moreover, by actuating the device according, the amount of pressure increase of the delayed exhalation may increase anywhere from, e.g., 1 to 30 cm $H_2O$, when the device is utilized.

Figure 14A:
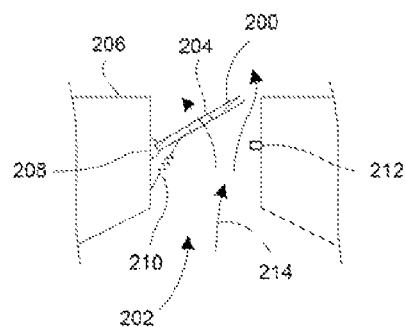
FIGS. 14A and 14B show side views of a variation of the valve assembly utilizing an electroactive polymer member which may stiffen when actuated.
Figure 14B:
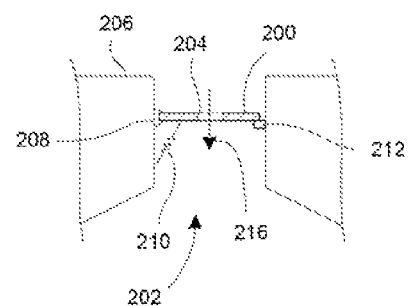

One example is shown in the side view of FIG. 14A which illustrates a variation of the valve assembly 196 where one or more flaps 200 may be connected to a frame or support 206 via a pivoting attachment 208, such as a pivot, living hinge, etc. The one or more flaps 200 may define an opening 204 through the flap 200 which has an opening size which is smaller than the passageway 202 covered by the entire flap 200. In its resting configuration, flap 200 may be biased via a biasing element 210 to remain closed over passageway 202 where the biasing element 210 may be an electroactive polymer. When the patient inhales, air may flow 214 through passageway 202, through opening 204, and flap 200 may configure into an open configuration allow the air to enter at a first flow rate 214. However, when the patient exhales, flap 200 may reconfigure into its closed configuration into rest against stop 212 such that the exhaled air is forced to exit through opening 204 at a decreased second flow rate 216, as shown in FIG. 14B. Biasing element 210 may be actuated by the application of energy to the element 210, e.g., on the order of milliwatts, to alter the stiffness of the biasing element 210 to thereby change the degree to which flap 200 may open and/or close to accordingly change the amount of air pressure required to open and/or close the flap 200 depending upon patient conditions and the treatment regimen desired.

Figure 15A:
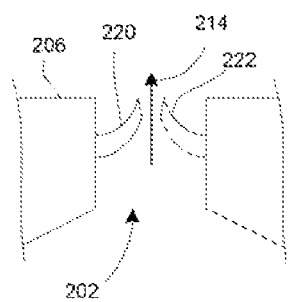
FIGS. 15A and 15B show side views of another variation of the valve assembly utilizing an electroactive polymer members configured as valve leaflets.
Figure 15B:
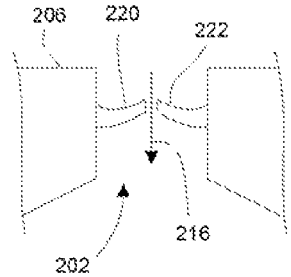

Another variation is shown in the side view of FIGS. 15A and 15B which illustrate two or more flap members 220, 222 which are flexible in their natural state such that the inflow 214 of air may enter at the first rate through an opening defined between the members. However, when actuated by the application of energy, the flap members 220, 222 may stiffen to reduce the size of the opening and thus allow the exhaled air to exit at a reduced rate relative to the inflow.

Figure 16A:
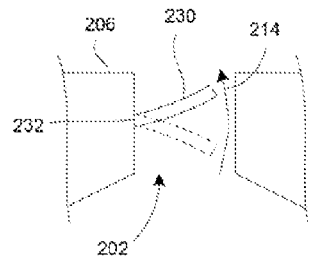
FIGS. 16A and 16B show side views of another variation of the valve assembly utilizing an electroactive polymer member configured as a cantilevered valve.
Figure 16B:
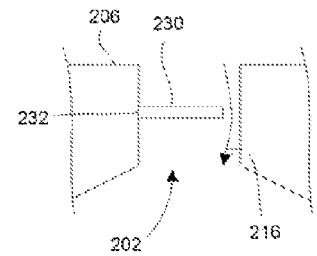

Another variation is shown in the side views of FIGS. 16A and 16B which show a cantilevered flap 230 which is attached 232 along the frame 206 such that the diameter or size of the flap 230 is less than the diameter or size of the passageway 202. The flap 230 may be comprised of an electroactive polymer which is flexible enough to allow for the inflow and outflow of air, as shown. When actuated by applying energy, flap 230 may stiffen to thus restrict the opening and thus allow for the restricted inflow and/or outflow of air through the space defined between the flap 230 and passageway 202, as shown in FIG. 16B.

Figure 17A:
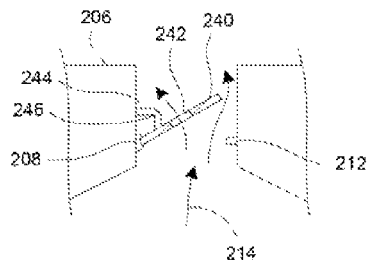
FIGS. 17A and 17B show side views of another variation of the valve assembly utilizing an electroactive polymer member configured as a pivoting member.
Figure 17B:
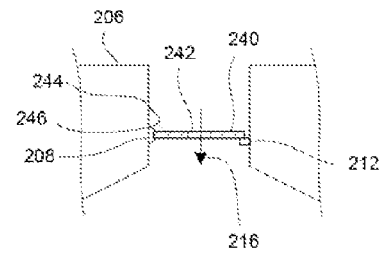

FIGS. 17A and 17B show yet another variation where the flap 240 may similarly define an opening 242 through the flap 240 itself. A restricting member 244 may be attached to both the frame 206 and flap 240 where the member 244 itself may have a pivoting portion 246, such as a pivot or living hinge, which allows the member 244 to bend about itself to allow for the opening and/or closing of the flap 240 relative to the passageway. When stiffened by the application of energy to the member 244, the flap 240 may be restricted in its movement to affect the exhalation and/or inhalation flow rate, as previously described.

Figure 18A:
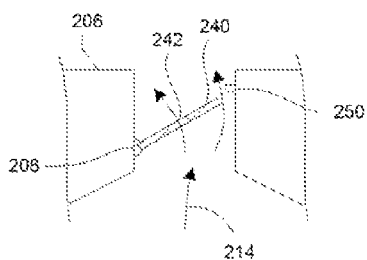
FIGS. 18A and 18B show side views of another variation of the valve assembly utilizing an electroactive polymer member configured with a slidable stop.
Figure 18B:
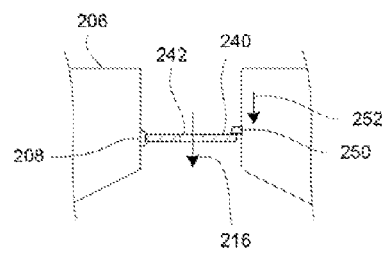
Figure 19A:
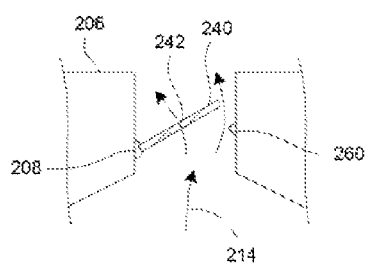
FIGS. 19A and 19B show side views of another variation of the valve assembly utilizing an electroactive polymer member configured with a pivoting stop.
Figure 19B:
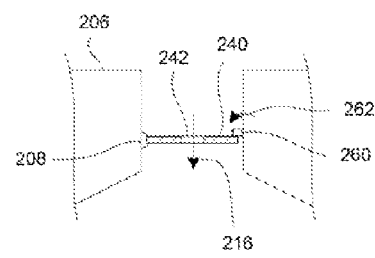

FIGS. 18A and 18B show yet another variation where stop 250 may be comprised of an electroactive polymer which may transition the stop 250 between an open and closed configuration. In the open configuration, the flap 240 is allowed to move freely when the stop 250 is moved out of interference from flap 240, as shown in FIG. 18A, while in the closed configuration the stop 250 is moved (indicated by the direction of movement 252) into a position which prevents flap 240 from further movement, as shown in FIG. 18B, thus requiring the outflow 216 to pass through the restricted opening 242. In yet another alternative, FIGS. 19A and 19B show a variation where the stop 260 may be actuated via an electroactive polymer to pivot, as indicated by the direction of movement 262, into an open and closed configuration when actuated to thereby allow flap 240 to move open or become restricted in its movement.

Figure 20A:
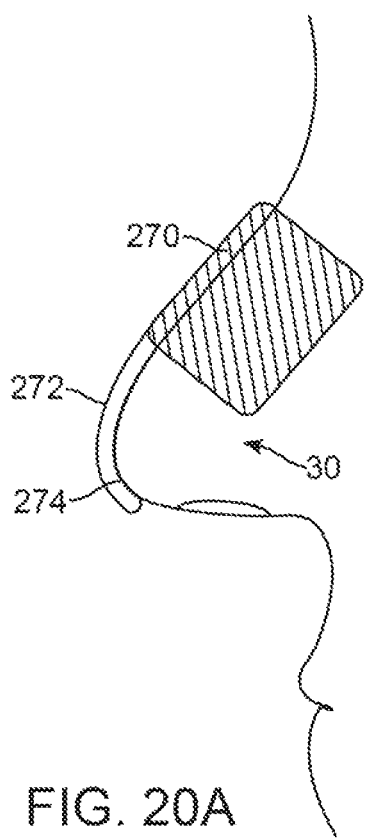
FIGS. 20A and 20B show side views of yet another variation where an actuating element may be configured to engage and retract the tip of the nose to facilitate or constrict airflow.
Figure 20B:
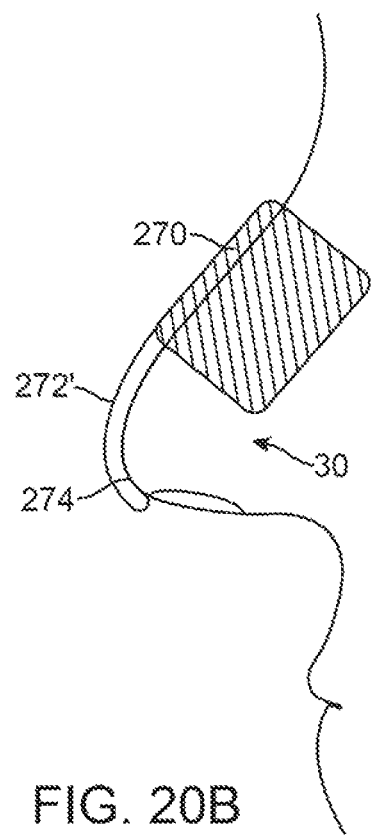

In yet another variation, FIGS. 20A and 20B show side view of restriction device 270 which may be adhered onto the patient's nose, as above. However, rather than device 270 constricting, it may function to anchor constricting member 272 which may extend along the nose and around the tip 274 of nose 30, as shown in FIG. 20A. For a patient with an otherwise constricted nasal passage, constricting member 272 (which may be comprised of a reconfigurable electroactive polymer) may be actuated to constrict such that member 272' may pull on the tip 274 of nose 30 to increase the airflow through the nasal openings 34.

Figure 21A:
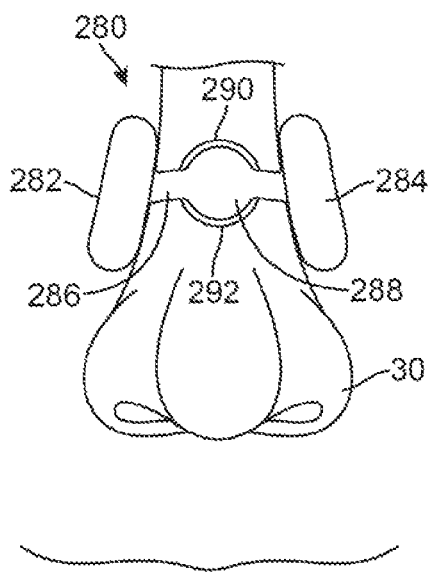
FIGS. 21A and 21B show front views of yet another variation where a fluid or gas may be actuated between a reservoir and respective restriction elements to partially constrict the airflow through the patient's nasal passages.
Figure 21B:
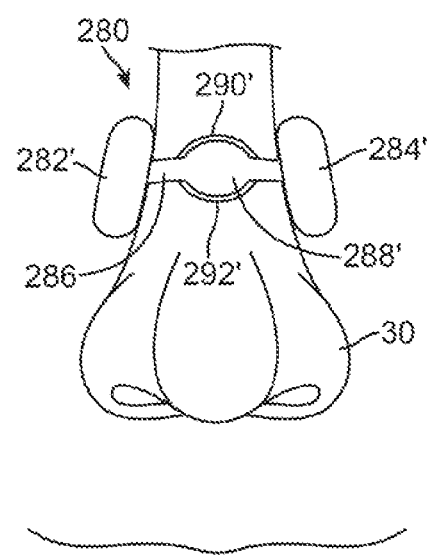

In another example, FIGS. 21A and 21B show restriction device 280 which utilizes a fluid or gas actuated between a reservoir 288 and inflatable respective first and second restriction elements 282, 284 to partially constrict the airflow through the patient's nasal passages. As shown in FIG. 21A, a fluid or gas reservoir 290 may be positioned along the bridging member coupling the inflatable restriction elements 282, 284. A fluid lumen 286 may connect the reservoir 290 with the restriction elements 282, 284 and first and/or second actuatable members 290, 292 may be positioned along a surface or within reservoir 288 such that when actuatable members 290', 292' are actuated to squeeze or constrict, the fluid contained within reservoir 288' may be forced or urged out and into the respective first and second inflated restriction members 282', 284', as shown in FIG. 21B, such that inflation of these members 282', 284' constrict the underlying nasal passages to induce the expiratory positive airway pressure. During inhalation, actuatable members 290, 292 may be relaxed to allow the fluid to flow back from the members 290, 292 into reservoir 288. To facilitate the fluid transfer, members 290, 292 may be made from a distensible material, such as latex, which may be inflated yet is biased to collapse to urge the fluid back into reservoir 288.

While illustrative examples are described above, it will be apparent to one skilled in the art that various changes and modifications may be made therein. Moreover, various apparatus or methods described above are also intended to be utilized in combination with one another, as practicable. The appended claims are intended to cover all such changes and modifications that fall within the true spirit and scope of the invention.

What is claimed is:

1. A method for restricting flow through a nasal passage, comprising:
   securing a bridging member over or upon an exterior surface of a patient's nose;
   monitoring respiratory activity of the patient through one or more cycles of unaltered respiration;
   actuating the bridging member to press upon the exterior surface of the nose such that an underlying nasal passage is at least partially constricted and exhalation is extended to result in an altered respiration;
   calculating a difference between the unaltered respiration and altered respiration; and,
   adjusting an actuation amount of the bridging member based upon the calculated difference.

2. The method of claim 1 wherein securing comprising positioning the bridging member over or upon the exterior surface via one or more support members positioned along either side of the nose.

3. The method of claim 1 wherein monitoring comprises sensing an inhalation volume.

4. The method of claim 3 wherein sensing comprises positioning one or more sensors in proximity to the nasal passage.

5. The method of claim 1 wherein monitoring comprises sensing exhalation activity by the patient.

6. The method of claim 1 wherein monitoring comprises recording the respiratory activity through at least five cycles of unaltered respiration.

7. The method of claim 1 wherein actuating comprises actuating the bridging member during exhalation by the patient.

8. The method of claim 1 further comprising ceasing actuation of the bridging member upon completion of exhalation by the patient.

9. The method of claim 1 wherein actuating comprises activating an electromechanical or electroactive polymer to press upon the exterior surface of the nose.

10. The method of claim 1 wherein actuating comprises constricting the bridging member from 1 to 10 mm.

11. The method of claim 1 wherein actuating comprising urging a fluid between a reservoir and at least one support member such that the underlying nasal passage is at least partially constricted.

12. The method of claim 1 wherein calculating comprises determining a difference in inhalation volume between the unaltered respiration and altered respiration.

13. The method of claim 1 wherein adjusting comprises increasing or decreasing the actuation amount based upon the calculated difference.

14. The method of claim 1 wherein adjusting comprises ramping the actuation amount.

15. The method of claim 1 wherein actuating comprises delaying actuation of the bridging member until a sleep disordered breathing event is detected.

* * * * *